United States Patent [19]

Sinofsky

[11] Patent Number: 5,725,522
[45] Date of Patent: *Mar. 10, 1998

[54] LASER SUTURING OF BIOLOGICAL MATERIALS

[75] Inventor: Edward L. Sinofsky, Dennis, Mass.

[73] Assignee: Rare Earth Medical, Inc., W. Yarmouth, Mass.

[*] Notice: The term of this patent shall not extend beyond the expiration date of Pat. No. 5,207,670.

[21] Appl. No.: 479,950

[22] Filed: Jun. 7, 1995

Related U.S. Application Data

[63] Continuation-in-part of Ser. No. 327,583, Oct. 24, 1994, Pat. No. 5,540,677, which is a continuation of Ser. No. 57,000, May 3, 1993, abandoned, which is a continuation-in-part of Ser. No. 804,791, Dec. 9, 1991, Pat. No. 5,207,670, which is a continuation-in-part of Ser. No. 538,977, Jun. 15, 1990, Pat. No. 5,071,417.

[51] Int. Cl.$^6$ ........................................ A61N 5/06
[52] U.S. Cl. ..................... 606/8; 606/229; 606/9; 606/144; 606/148
[58] Field of Search ........................ 606/2, 3, 8–17, 606/213–216, 219, 220, 144, 147, 148, 150, 228, 229; 607/88, 89; 604/304–306

[56] References Cited

U.S. PATENT DOCUMENTS

| 655,190 | 8/1900 | Bramson | 606/216 |
|---|---|---|---|
| 3,272,204 | 9/1966 | Artandi et al. | 128/334 |
| 3,988,782 | 11/1976 | Dradik et al. | 3/1 |

(List continued on next page.)

FOREIGN PATENT DOCUMENTS

| 0 214 712 | 3/1987 | European Pat. Off. |
|---|---|---|
| 0618 115 | 8/1978 | U.S.S.R. |
| 0618 116 | 8/1978 | U.S.S.R. |
| 1 091 933 | 5/1984 | U.S.S.R. |
| 2 108 282 | 5/1983 | United Kingdom |
| WO 92/12673 | 8/1992 | WIPO |

OTHER PUBLICATIONS

Barnes, N.P. et al. (1979) "TEM mode Ho: YLF laser" *SPIE* 190(LASL Optics Conference):297–304.

Grubbs, Jr., P.E. (1988) "Enhancement of $CO_2$ Laser Microvascular Anastomoses by Fibrin Glue" *J. Surgical Research* 45:112–119.

Hemmati, H. (1988) "Compact Ho: YLF Laser" *Nasa Tech Brief* 12(6) Item #154.

Kamiji, T. et al. (1989) "Microvascular anastomosis using polyethylene glycol–4000 and fibrin glue" *British J. Plastic Surgery* 42:54–58.

Oz, M.C. et al. (1989) "In Vitro Comparison of Thulium–Holmium–Chromium: YAG and Argon Ion Lasers for Welding of Biliary Tissue" *Lasers in Surgery and Medicine* 9:249–252.

Popp, H.W. et al. (1989) "Welding of Gallbladder Tissue With a Pulsed 2.15 μm Thulium–Holmium–Chromium: YAG Laser" *Lasers in Surgery and Medicine* 9:155–159.

(List continued on next page.)

*Primary Examiner*—Jennifer Bahr
*Assistant Examiner*—Stephen Huang
*Attorney, Agent, or Firm*—Thomas J. Engellenner; Lahive & Cockfield, LLP

[57] ABSTRACT

Methods and systems for endoscopic suturing of biological tissue are disclosed. Endoscopic instruments are described which serve to position a suture material at an anastomotic site and deliver laser radiation to the suture material to effect fusion. The suture material includes a structure adapted for positioning at an anastomotic site and has at least a portion of the structure formed by a photoreactive crosslinking agent, such that upon irradiation of the structure the crosslinking agent adheres to the biological material. In one embodiment, the suture material can also include a high tensile strength element which is coated with a laser activatable crosslinking agent or glue. Upon activation, the suture material creates a desired closure or joinder of the biological material and is left in place while the endoscope is advanced to another target site or removed.

16 Claims, 4 Drawing Sheets

U.S. PATENT DOCUMENTS

| | | | |
|---|---|---|---|
| 4,016,877 | 4/1977 | Cruz, Jr. et al. | 128/156 |
| 4,034,750 | 7/1977 | Seiderman | 128/155 |
| 4,143,660 | 3/1979 | Malyshev et al. | 128/303.1 |
| 4,316,467 | 2/1982 | Muckerheide | 128/303.1 |
| 4,641,650 | 2/1987 | Mok | 128/303.1 |
| 4,644,948 | 2/1987 | Lang et al. | 128/303.1 |
| 4,672,969 | 6/1987 | Dew | 128/397 |
| 4,719,912 | 1/1988 | Weinberg | 128/303.1 |
| 4,741,612 | 5/1988 | Birngruber et al. | 351/221 |
| 4,747,845 | 5/1988 | Korol | 604/368 |
| 4,799,479 | 1/1989 | Spears | 128/303.1 |
| 4,854,320 | 8/1989 | Dew et al. | 128/397 |
| 4,917,084 | 4/1990 | Sinofsky | 606/7 |
| 4,969,912 | 11/1990 | Kelman et al. | 623/66 |
| 4,990,151 | 2/1991 | Wallstén | 606/108 |
| 5,041,108 | 8/1991 | Fox et al. | 606/7 |
| 5,071,417 | 12/1991 | Sinofsky | 606/8 |
| 5,100,429 | 3/1992 | Sinofsky et al. | 606/195 |
| 5,156,613 | 10/1992 | Sawyer | 606/213 |
| 5,192,300 | 3/1993 | Fowler | 606/213 |
| 5,207,670 | 5/1993 | Sinofsky | 606/8 |
| 5,209,776 | 5/1993 | Bass et al. | 106/124 |

OTHER PUBLICATIONS

Poppas, D.P. et al (1988) "Laser Welding in Urethral Surgery: Improved Results with a Protein Soler" *J. Urology* 139:415–417.

Schober, R. et al. (1986) "Laser–Induced Alteration of Collagen Substructure Allows Microsurgical Tissue Welding" *Science* 232:1421–1422.

Yahr, W.Z. (1964) "Non–Occlusive Small Arterial Anastomosis with a Neodymium Laser" *Surgical Forum*.

LASER SUTURING OF BIOLOGICAL MATERIALS

REFERENCE TO RELATED APPLICATION

This application is a continuation-in-part of U.S. patent application Ser. No. 08/327,583 filed on Oct. 24, 1994, now U.S. Pat. No. 5,540,677 issued Jul. 30, 1996, which is a continuation of U.S. patent application Ser. No. 08/057,000, filed May 3, 1993, now abandoned Oct. 24, 1994 which is a continuation-in-part of U.S. patent application Ser. No. 07/804,791 filed Dec. 9, 1991, now U.S. Pat. No. 5,207,670 issued May 4, 1993, which is a continuation-in-part of U.S. patent application Ser. No. 07/538,977 filed Jun. 15, 1990, now U.S. Pat. No. 5,071,417 issued Dec. 10, 1991.

BACKGROUND OF THE INVENTION

The technical field of this invention is surgery and, in particular, endoscopic methods and materials for joining living tissues and promoting the healing of small biological structures.

The conventional approach to joining tissue segments following surgery, injury or the like, has been to employ mechanical sutures or staples. While these techniques are often successful, there are a number of limitations inherent in such mechanical approaches. First, the practice of suturing or stapling tissue segments together is limited by the eyesight and the dexterity of the surgeon which can present a severe constraint when anastomosing tiny biological structures. Second, when delicate biological tissues or organs are sutured, even minimal scarring can affect the function of the structure. Finally, suturing can be less than satisfactory, even when properly performed, because of the gaps which are left between the stitches, the inherent weakness of the joint, or the possibility of progressive structural weakening over time.

These problems are compounded during endoscopy, procedures which are performed with the objective of minimizing surgical invasiveness through the use of a tubular probe which permits the surgeon to "see" inside the patient and repair damaged tissue or otherwise treat diseases and/or traumatic conditions. Suturing during endoscopy has been a particularly difficult task.

Various researchers have proposed the use of laser energy to fuse biological tissues together. For example, Yahr et al. in an article in *Surgical Forum*, pp. 224–226 (1964), described an attempt at laser anastomosis of small arterial segments with a neodymium laser. However, the neodymium laser used by Yahr et al. operated at a wavelength of about 1.06 micrometers was not efficiently absorbed by the tissue, requiring large amounts of energy to effect fusion, while also affecting too large of a tissue volume.

Further research on laser fusion involving various alternative laser sources, such as the carbon dioxide laser emitting laser light at about 10.6 micrometers, the argon laser emitting light at about 0.50 micrometers, and the ruby laser emitting light at about 0.70 micrometers, continued to encounter problems in particular, the output of carbon dioxide lasers was found to be heavily absorbed by water and typically penetrated into water-laden tissue only to a depth to about 20 micrometers. This penetration depth and the resulting bond induced by carbon dioxide laser fusion was too shallow to provide durable bonding in a physiological environment.

Argon and other visible light lasers also produced less than satisfactory effects. The output of argon lasers and the like was found to be heavily absorbed by blood and subject to substantial scattering within the tissue. These effects combined to create a narrow therapeutic "window" between a proper amount of energy necessary for laser fusion and that which induces tissue carbonization, particularly in pigmented tissues and tissues that have a high degree of vascularization. Moreover, argon lasers have been particularly cumbersome devices, requiring large amounts of electricity and cooling water.

Recently, the development of new solid state laser sources have made prospects brighter for efficient, compact laser fusion systems suitable for clinical use. Such systems typically employ rare earth-doped yttrium aluminum garnet (YAG) or yttrium lithium fluoride (YLF) or yttrium-scadium-golilinium-garnet (YSGG) lasers. See, for example, U.S. Pat. Nos. 4,672,969 and 4,854,320 issued to Dew, disclosing the use of a neodymium-doped YAG laser to induce laser fusion of biological materials and to obtain deeper tissue penetration. However, even with such solid state laser sources, the problems of scattering and damage to adjacent tissue remain. The Dew patents disclose the use of computer look-up tables to control the laser dose based on empirical data.

The absorptive properties of biological structures differ considerably from one tissue type to another, as well as from individual to individual, making dosage look-up tables often unreliable. There exists a need for better methods and materials for accurately controlling the formation of anastomotic bonds which avoid thermal damage and achieve optimal results. In particular, non-mechanical suture materials which can take advantage of laser or other high energy light sources to join biological materials together or otherwise make repairs to delicate body tissues would satisfy a long-felt need in the art.

SUMMARY OF THE INVENTION

Methods and systems for endoscopic suturing of biological tissue are disclosed. Endoscopic instruments are described which serve to position a suture material at an anastomotic site and deliver laser radiation to the suture material to effect fusion. The suture material includes a structure adapted for positioning at an anastomotic site and has at least a portion of the structure formed by a photoreactive crosslinking agent, such that upon irradiation of the structure the crosslinking agent adheres to the biological material. In one embodiment, the suture material can also include a high tensile strength element which is coated with a laser activatable crosslinking agent or glue. Upon activation, the suture material creates a desired closure or joinder of the biological material and is left in place while the endoscope is advanced to another target site or removed.

The present invention can employ various "biological glue" materials as crosslinking agents in either solid, liquid, gel or powder form to form a bond to tissue segments and thereby hold them together while natural healing processes occur. The crosslinking agents should be biocompatible and are preferably biodegradable over time in vivo. Examples of such crosslinking agents include collagen, elastin, fibrin, albumin and various other photoreactive polymeric materials.

The terms "endoscope" and "endoscopic" are used herein to broadly encompass instruments such as laproscopes, cytoscopes, colonoscopes, sigmoidoscopes, arthroscopes, esophagoscopes, bronchoscopes, gastroscopes, thoracoscopes, peritoneoscopes, culdoscopes, catheters and the like, which are designed to penetrate a body structure, cavity or lumen and permit a clinician to view the internal body structure and effect a surgical procedure or other therapeutic action.

Various strength enhancing agents can also be incorporated into the suture structure to provide additional tensile support along and across the anasmmosis. Such high tensile strength elements can be formed from pre-crosslinked segments of the same material that forms the photoreactive crosslinking agent, or they can be formed from strips or fibers of other natural or synthetic biodegradable materials such as cotton or polyesters, to enhance the strength of the bond.

The present invention permits the creation of anastomoses of biological structures with the optimal use of appropriate laser energy, minimizing the total energy delivered to the site while obtaining maximum bond strength and integrity. The terms "anastomosis" and "anastomotic site" are used herein to broadly encompass the joinder of biological structures, including, for example, incision and wound healing, repair of blood vessels and other tubular structures, sealing of fissures, nerve repairs, reconstructive procedures, and the like.

The present invention is preferably practiced in conjunction with a high energy light source, such as laser, for delivery of a beam of radiation to an anastomotic site, and can also employ a reflectance sensor for measuring light reflected from the site and a controller for monitoring changes in the reflectance of the light from the site and controlling the laser in response to the reflectance changes.

In one embodiment, the laser radiation is delivered through an endoscopic instrument carrying at least one optical fiber. The instrument typically will further include an imaging system which consist of an optical fiber or series of lenslets to permit the user to view the distal end of the instrument. The instrument can also include one or more additional fibers for the delivery of illumination light or radiation from a laser diode (which can be broadband or white light or radiation from a laser diode) which is reflected and monitored by the reflectance sensor. Reflectance changes during the course of the suturing operation at one or more wavelengths can be monitored (or compared) to provide an indication of the degree of tissue crosslinking and determine when an optimal state of fusion has occurred.

The invention can be practiced using a conventional endoscope in which a probe-like photoreactive suturing assembly is inserted through the instrument channel of the endoscope to perform a suturing operation at an anastomotic site. The probe can include at least one optical fiber for delivery of fusion-inducing radiation and a means to deliver the suturing material to the site. Alternatively, the suturing assembly can be incorporated as an integral part of the endoscope and readily available to the surgeon without the need for removal of other instruments and insertion via the instrument channel. In yet another alternative, the suturing assembly can be constructed as a stand-alone instrument which is separately inserted into a patient and guided into position by endoscopic observation of the anastomotic site.

In the present invention, remote visualization and/or reflective feedback can also be used to monitor the state of crosslinking of the suture material with the biological material, as well as the degree of fusion or coagulation of the biological structures so as to allow an optimal dose by either manipulation of the energy level or exposure time, or by controlling the sweep of energy across an exposure path. Reflectance changes can also be employed by a control means in the present invention to adjust or terminate laser operation.

Various light sources can be employed to induce crosslinking, including gas, liquid and solid state laser media. Because the present invention permits the user to carefully monitor the energy dosage, solid state lasers can be utilized instead of the more conventional (and cumbersome) gas lasers. Such solid state laser include optically-pumped (e.g., lamp or diode pumped) laser crystals, diode lasers, and diode pumped optical fibers. Tunable laser sources can also be used to practical advantage in the present invention. In some applications, high intensity flash lamps can also be employed in lieu of a laser source. Since the feedback control systems disclosed herein eliminate (or reduce) the need for look-up tables, a tunable laser source can be used to full advantage by matching the laser output wavelength with the absorptive and/or dimensional characteristics of the biological structures to be repaired or otherwise joined. In one embodiment of the invention, the laser source can be tuned over at least a portion of a wavelength range from about 1.4 micrometers to about 2.5 micrometers to match particular tissue profiles.

In another aspect of the invention, a real-time display means is disclosed which can be incorporated into the endoscopic eyepiece or a video monitor used by the clinician during the procedure to provide a visual display of the state of tissue coagulation simultaneously with the viewing of the surgical site. The display can reveal reflectance values at one or more specific wavelengths (preferably, chosen for their sensitivity to the onset and optimal state of tissue crosslinking), as well as display a warning of the onset of tissue carbonization.

In one method, according to the invention, an endoscopic technique for photoreactive suturing of biological structures is disclosed in which laser energy is applied to join together two or more tissue segments via a suture structure that includes a photoreactive crosslinking agent, while the reflectance of light from the irradiated site is monitored. Changes in scattering due to crosslinking of the tissue and crosslinking agent will cause reflectance changes. The reflectance can be monitored in real-time to determine the optimal exposure duration or aid as visual feedback in the timing used in sweeping the energy across the anastomosis during the suturing procedure.

The method can further be enhanced by employing a suturing material which incorporates high tensile strength elements, and/or by coating the entire anastomotic site with a biological glue. The reinforcing strips provide load support across and along the repair line, and preferably are also bonded by the crosslinking agent to the tissue, itself, providing superior bond strength.

The depth of penetration of the laser energy can be controlled in one embodiment by tuning a mid-infrared laser along a range of wavelengths from about 1.4 micrometers to about 2.5 micrometers to adjust the penetration to match the desired weld depth. Tuning can be accomplished, for example, by mechanical or electro-optical variation in the orientation of a birefringent crystal disposed in the laser beam path.

This allows the clinician to select a weld depth appropriate to the size and type of structures to be welded. This feature of the invention can be particularly advantageous with delicate biological structures where accuracy is needed to crosslink only what is necessary for temporary strength, while avoiding thermal denaturing of critical structures that cannot function once scarred in most instances, the patient's body will metabolize the suture material over time simultaneous with (or following) the natural healing of the repair site by physiological processes.

DETAILED DESCRIPTION

Figure 1:
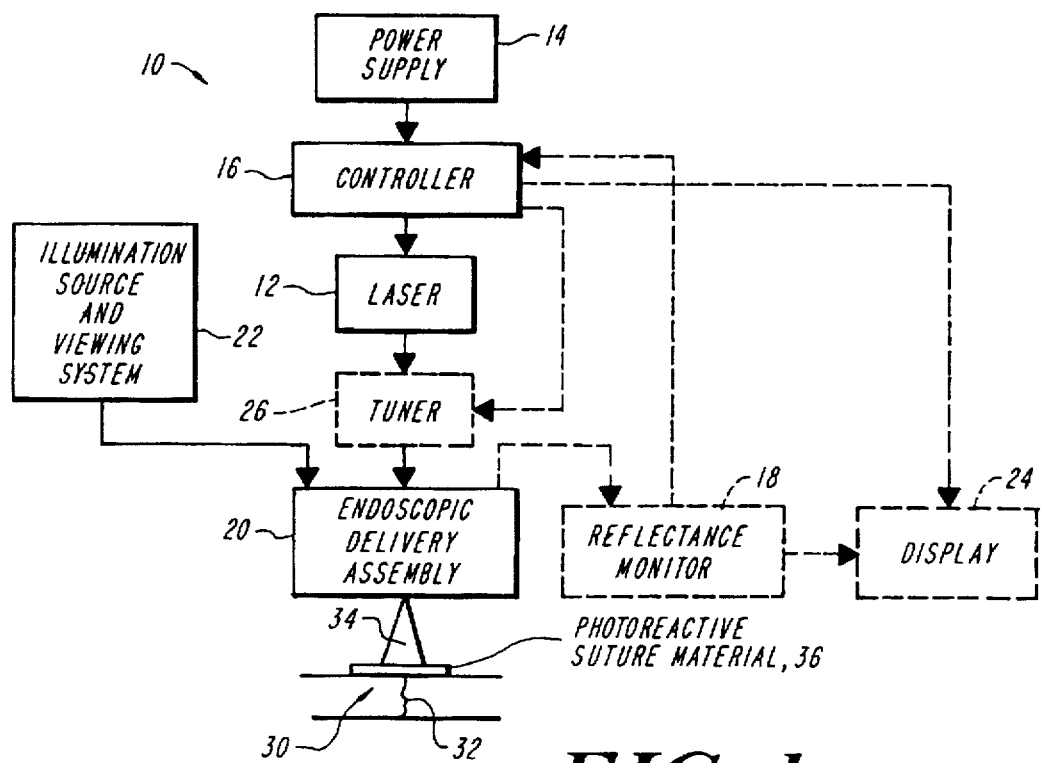
FIG. 1 is a schematic block diagram of a photoreactive suturing system according to the present invention.

In FIG. 1, a schematic block diagram of a photoreactive suturing system 10 is shown, including a laser 12, power supply 14, controller 16, endoscopic delivery assembly 20, illumination source and viewing system 22, and photoreactive suturing material 36. The system can further include a reflectance monitor 18, display 24 and tuner 26. In use, the output of laser 12 is delivered via the endoscope assembly 20, to an anastomotic site 30 to fuse the suture material 36 on opposite sides of a fissure or cleavage line 32 in a biological material. As the laser beam irradiates exposure zone 34, a crosslinking reaction occurs to fuse the suture material and the biological tissue in the vicinity of the site 30.

The degree of crosslinking can be determined by the reflectance monitor 18, which can provide electrical signals to controller 16 in order to control the procedure. The reflectance monitor 18 preferably receives light reflected by the site from a broadband or white light illumination source 22. In addition to controlling the laser operation automatically, the reflectance monitor 18 and/or controller 16 can also provide signals to a display 24 to provide visual (and/or audio) feedback to the clinical user, thereby permitting manual control. Tuner 26 can also be employed by the user (or automatically controlled by controller 16) to adjust the wavelength of the annealing radiation beam.

Figure 2:
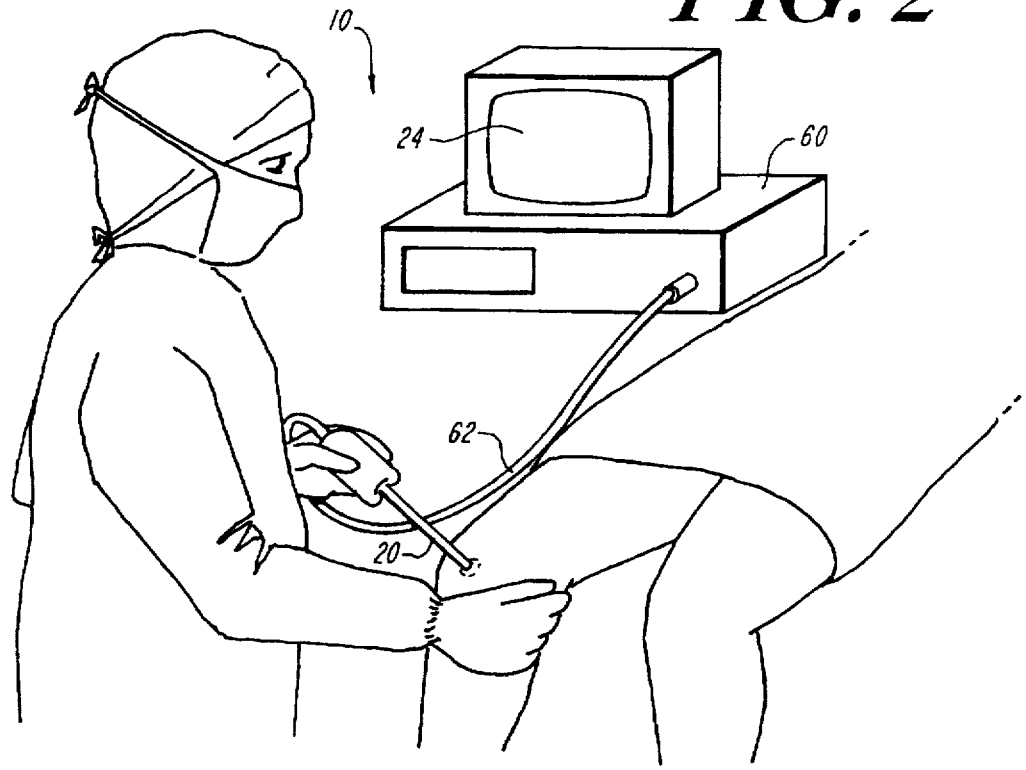
FIG. 2 is a perspective view of a clinical system embodying the principles of the invention.

FIG. 2 provides further schematic illustration of the photoreactive suture system 10 in use. The electrical and optical components of the system can be housed in a system cabinet 60 suitable for use in an operating room or other clinical environment. The laser output is delivered to the patient by an optical fiber cable 62 (which can include multiple optical fibers as detailed below) and an endoscope 20. The system is preferably used in conjunction with a video monitor 24 which is adapted to provide a visual display of the biological region at the tip of the endoscope to the user. The system and monitor 24 can also be designed to provide the user with data on progress of the crosslinking reaction.

Figure 3:
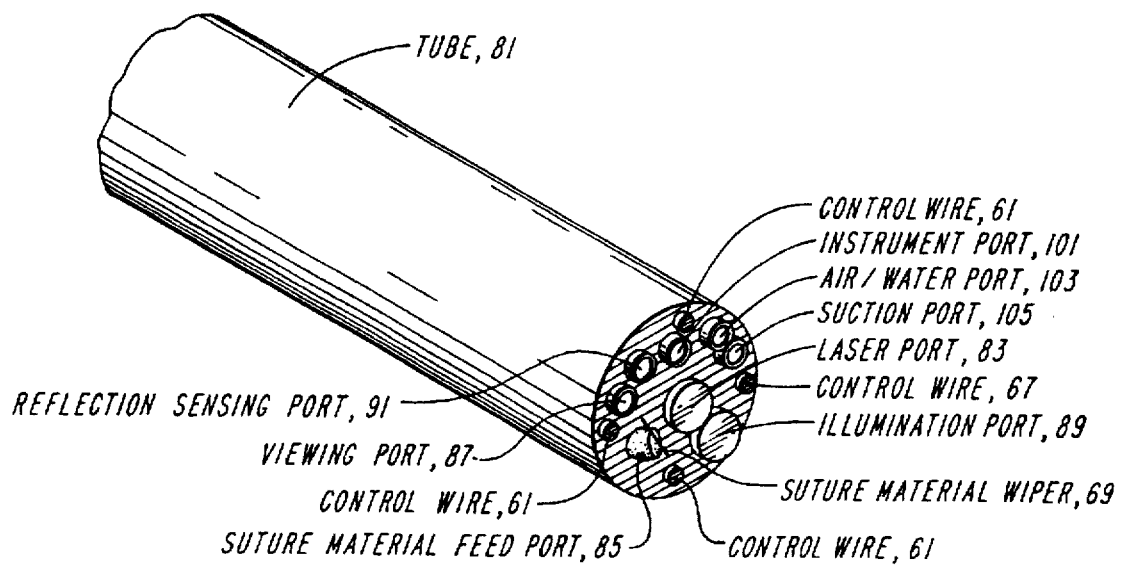
FIG. 3 is a front view of an endoscopic system incorporating the present invention.

In FIG. 3, a an endoscopic apparatus 81 for remote application of sutures according to the invention is shown. The apparatus 81 can be a catheter, arthroscope or other form of endoscope and disposed adjacent to a remote anastomotic site. Control wires 61 permit the clinician to twist, turn or otherwise maneuver the device to reach the desired site. As shown, apparatus 81 includes a suture material delivery port 85 and a laser port 83. The apparatus 81 can also include a viewing port 87, an illumination port 89 and a reflectance sensing port 91 to provide a display and monitoring of the crosslinking process, as described in more detail below. The apparatus 81 can further include an instrument channel 101, an air or water irrigation port 103, and a suction port 105.

Figure 4:
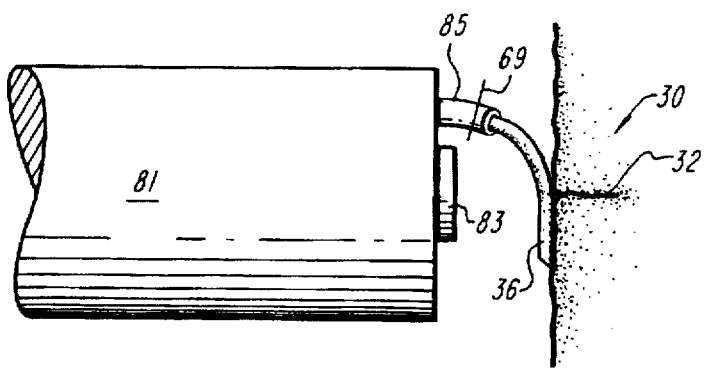
FIG. 4 is a side view of a simplified endoscopic system according to the invention.

In FIG. 4, an alternative embodiment is shown, simply consisting of a suture material delivery port 85 and a laser port 83 housed within a tubular casement 81. This instrument can be constructed small enough (e.g. less than about 2.0 micrometers) so that it can pass through a conventional endoscope instrument deliver channel.

As shown in FIG. 4, the suture port 85 delivers a photoreactive suture material 36 to the anastomotic site 30 where it can be draped across a fissure 32 or similar region requiring closure. The suture port can be equipped with a valve or wiper 69 to terminate or periodically stop the flow of suture material. The suture material comprises a structure with at least a portion of the structure formed by a crosslinking agent such that upon irradiation of said suture means the crosslinking agent adheres to the biological material and thereby provides closure at said anastomotic site. The laser means 83 provides the necessary light energy in the form of laser radiation to effect crosslinking of the suture material at the anastomotic site.

The suture materials of the present invention can take various forms. In the simplest embodiment, the suture material comprises a strip or strand of a photoreactive crosslinking agent, such a collagen fibers, which can be injected into, or draped upon, a fissure or incision and then crosslinked to the tissue to provide closure. Once in place, the suture material is irradiated with laser or other high intensity light energy to fuse the suture to the anastomotic site.

Figure 5:
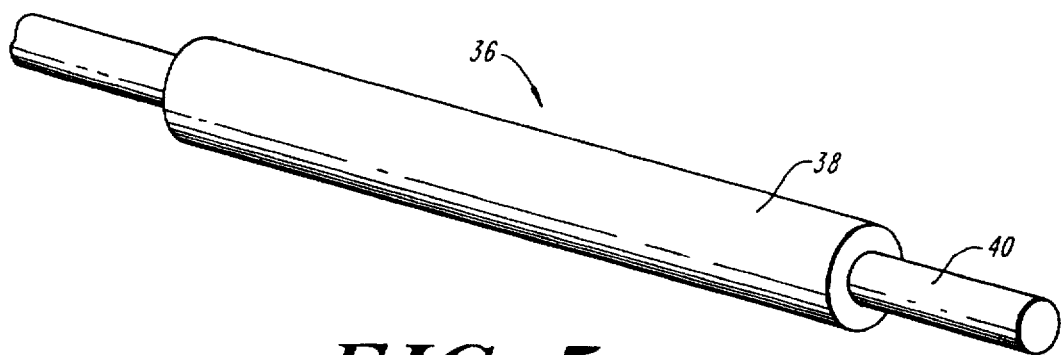
FIG. 5 is a schematic illustration of a suture material incorporating a high tensile strength element according to the invention.

Alternatively, as shown in FIG. 5, the suture material 36 can include a high tensile strength core element 40 and an outer cross-linkable agent 38 which are likewise used to sew or drape the anastomotic site prior to irradiation and fusion.

The present invention can employ various materials as crosslinking agents in either solid, liquid, gel or powder form to form a bond to tissue segments and thereby hold them together while natural healing processes occur. The crosslinking agents should be biocompatible and are preferably biodegradable over time in vivo. Examples of such crosslinking agents include collagen, elastin, fibrin, albumin and various other photoreactive polymeric materials.

Various strength enhancing agents can also be incorporated into the suture structure to provide additional tensile support along and across the anastomosis. Such high tensile strength elements can be formed from pre-crosslinked segments of the same material that forms the photoreactive crosslinking agent, or they can be formed from strips or fibers of other natural or synthetic biodegradable materials such as polyesters, to enhance the strength of the bond.

The present invention can be practiced with a wide variety of laser sources, including both gas and solid state lasers, operating in either continuous wave ("c.w.") or pulsed modes. More specifically, the laser sources can be carbon monoxide, carbon dioxide, argon lasers or various excimer lasers utilizing mixtures of halogen and noble gases, such as argon-fluoride, krypton-fluoride, xenon-chloride and xenon-fluoride. Additionally, the laser can be a solid state laser employing a rare, earth-doped Yttrium Aluminmn Garnet (YAG) or Yttrium Lithium Fluoride (YLF) or a Yttrium-Scandium-Gadolinium-Garnet (YSGG) laser.

In one preferred embodiment, the laser source is a rare, earth-doped, solid state laser, such as a holmium-doped, erbium-doped or thulium-doped solid state laser of the YAG, YLF or YSGG type which can be operated in a low wattage c.w. or pulsed mode with an output wavelength in the range of about 1.4 to about 2.5 micrometers and a power density of about 0.1 watt/mm$^2$ to about 1.0 watt/mm$^2$. Such laser sources are disclosed in U.S. Pat. No. 4,917,084 issued on Apr. 17, 1990, to the present inventor and incorporated herein by reference.

The absorption of laser energy from such solid state laser sources by biological tissues is relatively high in relation to the absorption of such energy by water, thereby providing an absorption length in the subject's body of about 100 microns or more. Thus, it is possible to operate satisfactorily even with 10–20 micrometers of blood between the handpiece tip and the anastomotic site.

Figure 6:
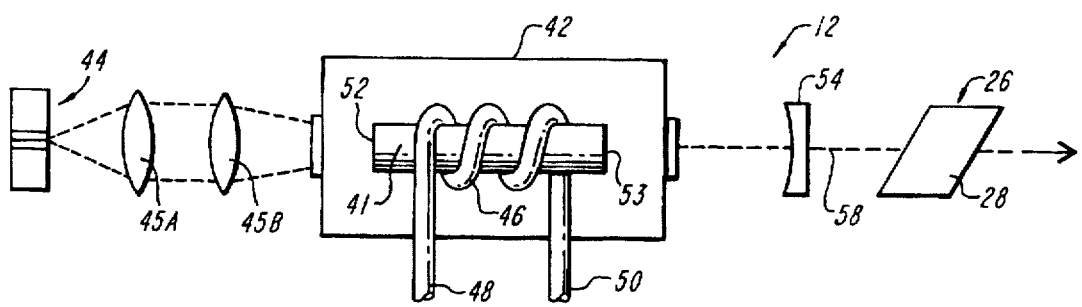
FIG. 6 is a more detailed schematic diagram of a laser source useful in the system of FIG. 1.

FIG. 6 is a schematic illustration of laser source 12, including a solid-state laser crystal 41, vacuum chamber 42 and diode pump source 44. The laser crystal 41 is preferably surrounded by a cooling quartz or fused-silica jacket 46 having inlet pipe 48 and an outlet pipe 50 for circulation of liquid nitrogen or other cryogenic coolant. The laser cavity can be formed by input crystal face coating 52 and partially-reflective output mirror 54.

Generally, the laser crystal 41 is excited by optical pumping, that being, irradiation of the crystal with light from the laser diode 44. (The diode 44 can be cooled by a pumped coolant or employ a heatsink). Both ends of the laser crystal 41 are preferably polished flat. The input face of the crystal 41 is preferably finished with a coating 52 for high transmittance at the pump wavelength and high reflectance of the output wavelength. The other end of the crystal 41 preferably includes an anti-reflective coating 50 for high transmittal of the output wavelength. The entire cavity of the reflector preferably is evacuated to provide thermal insulation and avoid moisture condensation.

For further details on the construction of cryogenic, solid-state lasers, see, for example, an article by Barnes et al., Vol. 190, *Society of the Photo-Optical Instrumentation Engineers*, pp. 297–304 (1979), NASA/JPL Technical Brief No. NPO-17282/6780 by Hemmati (June, 1988) and above-referenced U.S. Pat. No. 4,917,084, all of which are herein incorporated by reference.

Also shown in FIG. 6 is a tuning element 26 which can include, for example, a birefringent crystal 28 disposed along the beam path 58 at a slight offset from Brewster's angle. The crystal 28 can be tuned electro-optically by application of a voltage, as shown schematically. Alternatively, the laser wavelength can be tuned mechanically by tilting or rotating the crystal 28 relative to the beam path using techniques well known in the art.

Figure 7:
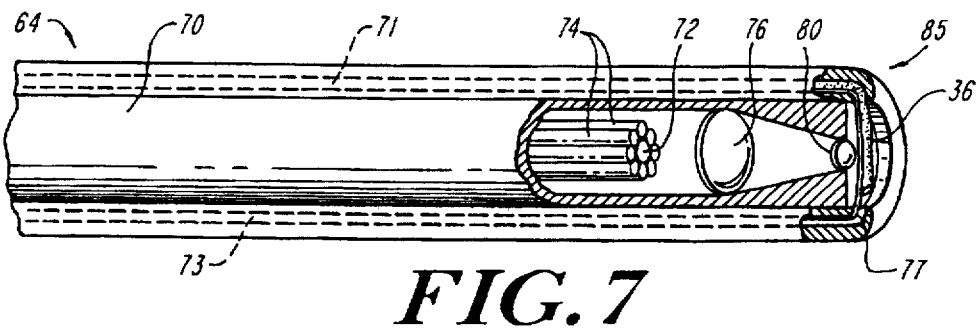
FIG. 7 is a partial, cross-sectional view of a laser beam delivery assembly according to the invention.

In FIG. 7, a partial, cross-sectional side view of another suturing assembly 64 is shown, adapted for passage through an endoscopic instrument channel or another application (such as incorporation into other systems or hand-held instruments). The assembly 64 includes a casing 70 for at least one optical fiber and a suture material delivery means 71. The assembly can further include a return conduit 73 for advancing the suture material 36 and aligning the material in the path of the radiation. As shown, the suture material 36 is delivered via port 85 to the anastomotic site. The suture material can be strung across the face of lens 80 (aligned, for example, by a groove or guide in the distal end face of the instrument 64) such that irradiation causes the suture material to crosslink with biological tissue at the site and thereby effect closure. The suture material 36 can further include a nonreactive component 77 (e.g. a string or optically transparent backing) that is preserved following fusion, such that the component 77 can be drawn into the return conduit 73 and thereby advance another portion of the suture material into position to effect another weld.

Figure 8:
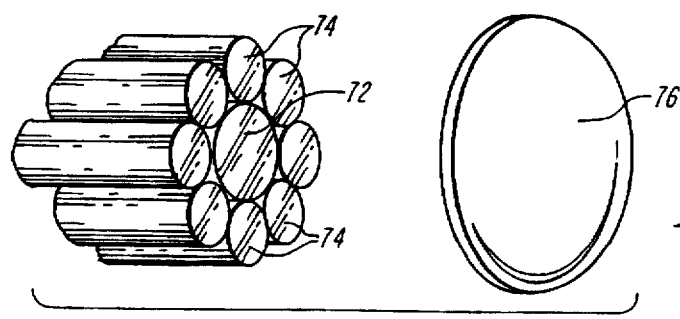
FIG. 8 is a front view of the laser delivery handpiece of FIG. 7.

With further reference to FIG. 8 as well, the assembly 64 serves to deliver laser irradiation suitable for fusion of the suture material and/or biological tissue via a central optical fiber 72 connected to laser source, as well as one or more additional illumination fibers 74 for the delivery of illumination light and the transmittal of reflected light. The surgical laser delivery fiber 72 is preferable a low hydroxyl ion content silica fiber. As shown in FIG. 8, the assembly 64 can deliver illumination light via fibers 74. In one embodiment, these fibers 74 can also be used to collect reflective light and deliver it to a controller. Alternatively, some of the fibers 74 can be devoted entirely to collection of reflected light. The handpiece 64 can further include one or more lens elements 76, as well as a transparent protective cover element or terminal lens 82.

Figure 9:
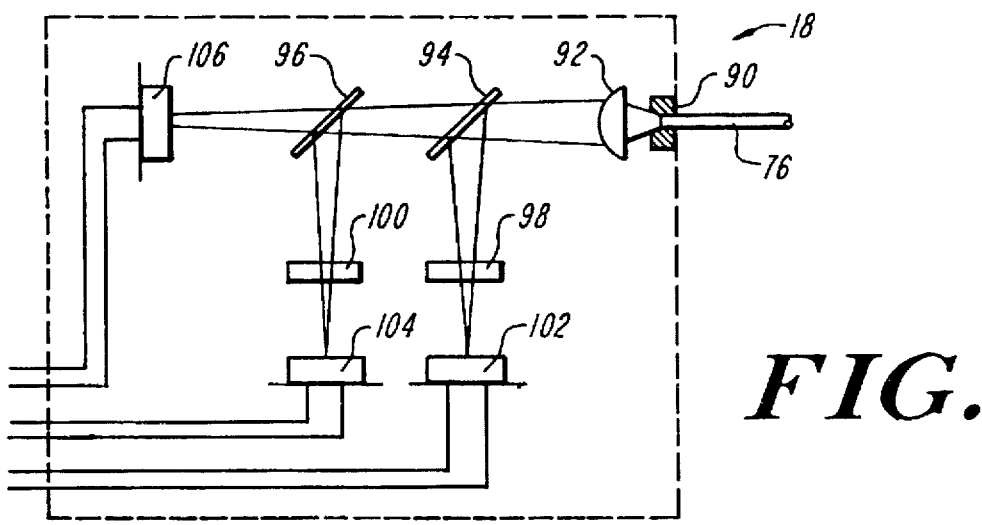
FIG. 9 is a more detailed schematic diagram of reflectance monitor for use in the present invention.

FIG. 9 is a more detailed schematic diagram of a reflectance monitor 18, including a coupling port 90 for coupling with one or more fibers 76 to receive reflectance signals from the instruments of FIGS. 3, 4, 7 and/or 8. The reflectance monitor 18 can further include a focusing lens 92 and first and second beam splitting elements 94 and 96, which serve to divide the reflected light into 3 (or more) different beams for processing.

As shown in FIG. 9, a first beam is transmitted to a first optical filter 98 to detector 102 (providing, for example, measurement of reflected light at wavelengths shorter than 0.7 micrometers). A second portion of the reflected light signal is transmitted by beam splitter 96 through a second optical filter 100 to detector 104 (e.g., providing measurement of light at wavelengths shorter than 1.1 micrometers). Finally, a third portion of the reflected light is transmitted to photodetector 106 (e.g., for measurement of reflected light at wavelengths greater than 1.6 micrometers). Each of the detector elements 102, 104, and 106 generate electrical signals in response to the intensity of light at particular wavelengths.

The detector elements 102, 104 and 106 preferably include synchronous demodulation circuitry and are used in conjunction with a modulated illumination source to suppress any artifacts caused by stray light or the ambient environment.

It should be apparent that other optical arrangements can be employed to obtain multiple wavelength analysis, including the use, for example, of dichroic elements, either as beamsplitters or in conjunction with such beamsplitters, to effectively pass particular wavelengths to specific detector elements. It should also be apparent that more than three discreet wavelengths can be measured, depending upon the particular application. The signals from the detector elements can then be transmitted to a controller and/or a display element (as shown in FIG. 1).

In the controller, signals from the reflectance monitor are analyzed (as detailed below) to determine the degree of crosslinking which is occurring in the suture material and/or in the biological tissue exposed to the laser radiation. Such analysis can generate control signals which will progressively reduce the laser output energy over time as a particular site experiences cumulative exposure. The control signals can further provide for an automatic shut-off of the laser when the optimal state of crosslinking has been exceeded and/or the onset of carbonization is occurring.

Figure 10:
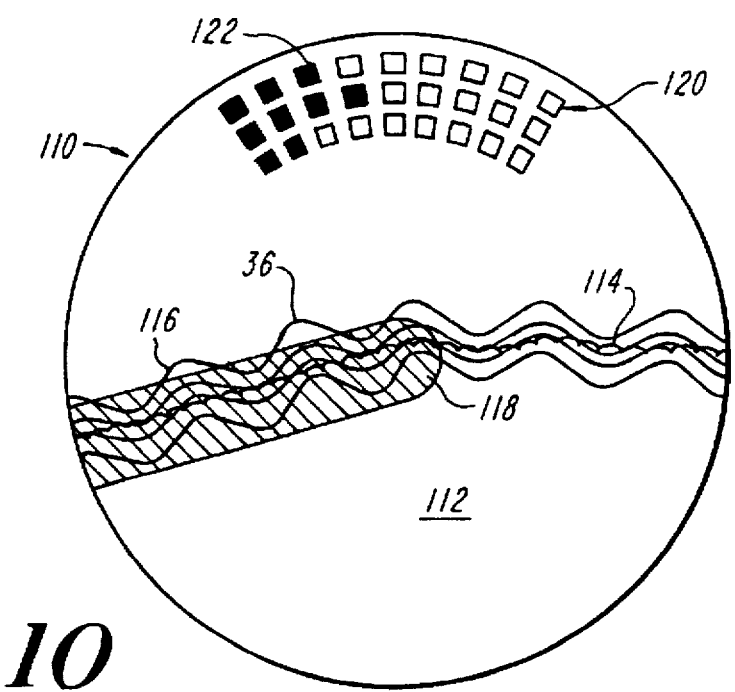
FIG. 10 is a schematic illustration of a clinical video monitor view displaying reflectance measurements according to the invention.

As shown in FIG. 10, the data from the reflectance monitor can also be provided directly to the clinician. In FIG. 10, a simulated view from a video monitor 110 is shown in which the field of view 112 includes a fissure or cleavage line 114 dividing separate bodies at an anastomotic site. Also shown within the field of view is the suture material 36 which has already been draped along the fissure, a fusion track 116 which has been formed by laser radiation, and a present exposure zone 118. Also shown by the monitor 110 is a display of the reflectance values for the reflectance monitor of FIG. 9, including illuminated warning lights 122 which serve to indicate the reflectance intensity at particular wavelengths or other optical data indicative of the degree of crosslinking and/or tissue fusion.

In use, the apparatus of the present invention can be employed to analyze the degree of crosslinking by comparing the reflectance ratios of a site at two or more wavelengths. Preferably, intensity readings for three or more wavelength ranges are employed in order to accurately assess the degree of crosslinking and to ensure that the optimal state is not exceeded. The particular wavelengths to be monitored will, of course, vary with the particular tissue undergoing treatment. Although the tissue type, (e.g., blood-containing tissue or that which is relatively blood-free) will vary, the general principles of the invention, as disclosed herein, can be readily applied by those skilled in the art to diverse procedures in which the fusion of biological materials is desired.

For example, it is known that carbonization of many tissue types is accompanied by a decrease in visible light reflectance and an increase in infrared reflectance. Thus, the analyzing circuitry of the controller can be constructed to provide a warning (or automatically shut off the laser radiation) when darkening in the visible wavelengths occurs or when the ratio of visible to infrared values falls below a predefined level.

Moreover, when the material to be joined (e.g., aortic tissue) is relatively unpigmented, reliance on changes in the reflectance of visible light can be inaccurate, but infrared reflectance changes (e.g., above 1.1 micrometers) can reliably indicate the degree of crosslinking. (Lack of change in the visible reflectance is one of the reasons that tissues of this type are difficult to crosslink, as no change in the target's visible properties are observed until the tissue is overexposed to laser energy.) Consequently, the analyzing circuitry can monitor infrared reflectance changes (e.g., greater than about 1.0 micrometers) as an indicator of proper crosslinking.

Finally, the reflectance sensor can also be used as a proximity monitor to ensue that the laser is in fact disposed at a proper distance from the anastomic site. By measuring total reflectance (over the entire visible-infrared range or a portion thereof), a sudden drop in the reflectance value will typically be related to incorrect placement of the handpiece.

Thus, the analyzing circuitry can sense the changes in reflectance and generate a warning to the user (or automatically shut off the system) until proper placement is achieved.

What is claimed:

1. An apparatus for joining biological materials comprising:

a suture means for delivering a photoreactive suture material to an anastomotic site, the suture material comprising a crosslinking agent such that upon irradiation of said suture means the crosslinking agent adheres to the biological material;

laser means for delivering laser radiation to said anastomotic site to activate the crosslinking agent and induce bonding of the suture material to the biological material, thereby providing a suture between segments of biological material; and a tubular casement, housing at least a portion of both the suture means and the laser means to facilitate delivery of the suture material and radiation.

2. Apparatus according to claim 1 wherein the apparatus has a diameter less than about 2.0 micrometers to permit insertion into an instrument channel of an endoscope.

3. Apparatus according to claim 1 wherein the casement is an endoscope and the suture means and the laser means form integral parts of the endoscope.

4. Apparatus according to claim 1 wherein said suture means further comprises a structure which is biodegradable over time in vivo.

5. Apparatus according to claim 1 wherein the crosslinking agent comprises at least one agent chosen from the group consisting of collagen, elastin, fibrin and albumin.

6. Apparatus according to claim 1 wherein the suture material further comprises a crosslinking agent and at least one high tensile strength element which inhibits tears in said suture material.

7. Apparatus according to claim 6 wherein the high tensile strength element is connected to said cross-linking agent, such that, upon irradiation, the high strength element and biological material are joined to each other to enhance bond strength.

8. Apparatus according to claim 1 wherein the laser means further comprises a laser generating an output wavelength ranging from about 1.4 to about 2.5 micrometers.

9. Apparatus according to claim 1 wherein the apparatus further includes analyzing means for determining the degree of crosslinking within an exposure zone based on said plurality of reflectance intensity measurements at distinct wavelengths.

10. Apparatus according to claim 1 wherein the laser means further comprises at least one low hydroxyl ion content silica fiber within the casement to deliver laser radiation to the site.

11. A method for joining biological material comprising:

endoscopically delivering a suture material to an anastomotic site, the suture material comprising a photoreactive crosslinking agent; and endoscopically delivering light energy to said site such that upon irradiation of said suture material with said light energy the crosslinking agent adheres to the biological material and thereby provides closure at said anastomotic site.

12. The method of claim 11 wherein the method further comprises measuring light reflected from said site; and controlling the laser in response to monitored changes in the reflectance of the light from the site to achieve crosslinking of the biological materials without thermal damage.

13. The method of claim 11 wherein the method further comprises tuning the output wavelength of the beam of laser radiation to match the characteristics of the crosslinking agent or the biological materials.

14. The method according to claim 11 wherein the method further comprises analyzing the degree of crosslinking within an exposure zone based on measurements of reflectance intensity at a plurality of wavelengths.

15. The method of claim 11 wherein the method further comprises applying a suture material having at least one high tensile strength element which inhibits tears in said structure.

16. The method of claim 15 wherein the high tensile strength element is connected to said cross-linking agent, such that, upon irradiation, the high strength element and biological material are joined to each other to enhance bond strength to the anastomotic site prior to laser irradiation.

* * * * *